United States Patent [19]

Schultz

[11] Patent Number: 4,707,534

[45] Date of Patent: Nov. 17, 1987

[54] GLYCIDYLETHERS OF FLUORENE-CONTAINING BISPHENOLS

[75] Inventor: William J. Schultz, Vadnais Heights, Minn.

[73] Assignee: Minnesota Mining and Manufacturing Company, St. Paul, Minn.

[21] Appl. No.: 939,574

[22] Filed: Dec. 9, 1986

[51] Int. Cl.$^4$ ............................................. C08G 59/24
[52] U.S. Cl. ...................................... 528/97; 549/560
[58] Field of Search ........................... 528/97; 549/560

[56] References Cited

U.S. PATENT DOCUMENTS

| | | | |
|---|---|---|---|
| 2,902,471 | 9/1959 | Bruin ...................................... | 260/47 |
| 3,298,998 | 1/1967 | McConnel ............................. | 260/47 |
| 3,332,908 | 7/1967 | Sellers ................................... | 260/47 |
| 3,355,511 | 11/1967 | Schwarzer ........................ | 528/97 X |
| 3,410,825 | 11/1968 | Coover et al. .......................... | 528/97 |
| 3,635,843 | 1/1972 | Parry et al. ............................ | 528/97 |
| 3,795,658 | 3/1974 | Thompson et al. .................... | 528/97 |
| 4,331,582 | 5/1982 | Babayan .............................. | 523/453 |

OTHER PUBLICATIONS

U.S. Ser. No. 830,552, filed Feb. 18, 1986.

Primary Examiner—Earl Nielsen
Attorney, Agent, or Firm—Donald M. Sell; James A. Smith; Lorraine R. Sherman

[57] ABSTRACT

Diglycidyl ethers of ortho-substituted-4-hydroxyphenylfluorenes, curable compositions comprising the diglycidyl ethers, and cured resins thereof have a high glass transition and an improved modulus of elasticity. The diglycidyl ethers of the invention for use in the curable composition of the invention can be mixtures obtained by the reaction of epihalohydrin with mixtures of fluorenebisphenols obtained by the reaction of one mole of one or more fluorenones with two or more moles or mixtures of two or more ortho-substituted phenols. The compositions are useful in molding and coating applications and in composite articles where the operating temperature of the article or material is elevated.

14 Claims, No Drawings

GLYCIDYLETHERS OF FLUORENE-CONTAINING BISPHENOLS

TECHNICAL FIELD

This invention relates to aromatic polyepoxides and a method of their preparation. In another aspect, it discloses compositions containing these polyepoxides (ethers) that can be cured to resin products having high glass transition temperature and improved modulus of elasticity.

BACKGROUND OF THE INVENTION

Epoxy resins are monomers or prepolymers that react with curing agents to yield high-performance resins. These resins have gained wide acceptance as protective coatings, electrical insulation, structural adhesives, and in structural applications as a matrix resin for composites because they possess a combination of characteristics such as thermal and chemical resistance, adhesion, and abrasion resistance.

Epoxy resins are characterized by the presence of a 3-member cyclic ether group commonly referred to as an epoxy, 1,2-epoxide or an oxirane group. The epoxy resins are cured, or caused to harden, by the addition of a curing or hardening agent. Curing agents used include anhydrides, amines, polyamides, Lewis acids, salts and others. The most common class of epoxy resins are diglycidyl ethers that can be cured by the use of polyamino compounds.

Epoxy resins are frequently required to have high glass transition temperatures in order to have structural properties at high temperatures. A method of achieving high glass transition temperatures in epoxy resins is to prepare resins having high crosslink density and a high concentration of polar groups. This technique is disclosed in U.S. Pat. No. 4,331,582, wherein it is taught that bis[4-(N-N-diglycidylamino)-phenyl]methane (TGDDM) is cured with di(4-aminophenyl)sulfone (DDS). While this method does produce resins that have high glass transition temperatures, the resins have several shortcomings. The materials are very brittle and suffer a large loss in glass transition temperature when exposed to moisture. These problems are caused by the high crosslink density and high concentration of polar groups respectively. DDS can also be used to cure other epoxy resins such as glycidyl ethers of polyhydric phenols. Again, while these resins may be characterized by high glass transition temperatures, they also tend to be very brittle.

Epoxy resin compositions in which the epoxy group-containing compound contains a polycyclic structure and which can be cured to resins having a high glass transition temperature are known. Examples of such resin compositions among others are the glycidyl ethers of polyhydroxy-phenylchroman disclosed in U.S. Pat. No. 2,902,471 and the bisglycidyl ethers of polycarbocyclic substituted bisphenols, e.g., (2-norcamphanylidene)diphenol, described in U.S. Pat. No. 3,298,998; the bisglycidyl ethers of cyclopentenyl substituted bisphenols disclosed in U.S. Pat. No. 3,332,908; and the glycidyl ethers of 9,9-bis(4-hydroxyphenyl)-fluorene described in assignee's copending patent application U.S. Ser. No. 830,552, filed Feb. 18, 1986. Although these compositions can be cured using conventional curing agents to resins having a high glass transition temperature, compared to the cured resins of the instant invention, they have a low stiffness as expressed by modulus of elasticity. As is known in the art the chemical structure and ring numbering system of the fluorene compound is as follows:

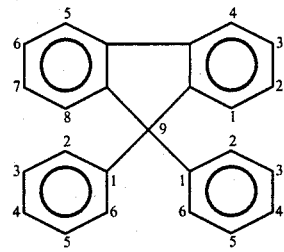

SUMMARY OF THE INVENTION

Briefly, the present invention provides diglycidyl ethers of ortho-substituted-4-hydroxyphenylfluorenes, curable compositions comprising the diglycidyl ethers, and cured resins thereof having a high glass transition and an improved modulus of elasticity. The modulus of elasticity at 20° C., however, can be as low as 2.0 or lower when the composition is toughened by the incorporation into the curable composition of a rubbery heterophase.

The modulus of elasticity at 20° C. of the cured resin of the invention preferably is at least 2.50 GPa, and most preferably it is at least 2.85 GPa.

Universal agreement of the terminology to be used in the field of epoxy resins has not been reached. The term "epoxy resin" has been used to indicate not only any molecule containing at least one group having a three-membered ring of which one member is oxygen but also both the uncured and cured compositions containing such a molecule. Within this application, the term "polyepoxide" means a molecule that contains more than one

group and the term "aromatic polyepoxide" means a molecule that contains more than one that are one

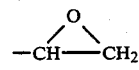

group that are attached directly or indirectly to an aromatic nucleus such as a benzene, diphenyl, diphenylmethane, diphenylpropane, or naphthalene nucleus, etc. The term "epoxy resin composition" will be used to indicate uncured compositions comprising a polyepoxide, curing agents, and other components that can be cured to a "cured epoxy resin". The curable composition aspect of the invention therefore comprises:

(a) one or more aromatic polyepoxides of which at least 25 percent by weight is at least one glycidyl ether of an ortho-substituted-4-hydroxyphenylfluorene and (b) one or more epoxy curing agents for curing the epoxy composition.

DETAILED DESCRIPTION

The glycidyl ethers of ortho-substituted-4-hydroxyphenyl-fluorenes are preferably any 9,9-bis(4-hydroxyphenyl)fluorenes that have at least one ortho-substituting group, e.g. a 3- or 5-substituting group that is inert in the polymerization of epoxy group-containing compounds, and has an epoxy equivalent weight of at most about 500. Preferably, the glycidyl ethers of the invention are compounds having the formula

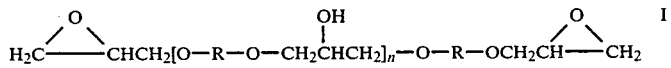

wherein
n is zero or a number having a value of 1 to 3, preferably, n is zero, and
R is a divalent organic group having the formula

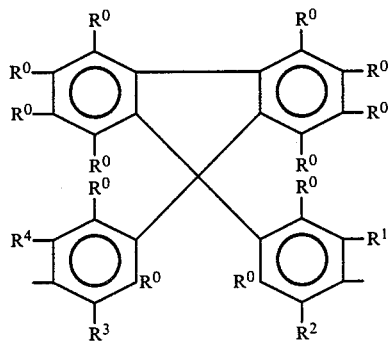

in which
each $R^0$ is independently selected from hydrogen and groups that are inert in the polymerization of epoxide group-containing compounds which are preferably selected from halogen, linear and branched alkyl groups having 1 to 6 carbon atoms, phenyl, nitro, acetyl, and trimethylsilyl; and
each of $R^1$, $R^2$, $R^3$, and $R^4$ is independently selected from hydrogen, linear and branched alkyl groups having 1 to 6 carbon atoms, phenyl and halogen;
with the privisos that at least one of $R^1$, $R^2$, $R^3$, and $R^4$ is a linear or branched alkyl group having 1 to 6 carbon atoms, a phenyl group, or halogen and the epoxy equivalent weight of the diglycidyl ether is at most about 500.

The curable composition of the invention must contain at least 25 percent by weight (i.e., 25 to 100 weight percent), preferably 50 to 100 weight percent, of the above defined glycidyl ether and up to 75 percent, preferably 0 to 50 weight percent, by weight of other aromatic polyepoxides. Such aromatic polyepoxides are well known and are compounds in which there is present at least one aromatic ring structure, e.g. a benzene ring, and more than one epoxy group, e.g

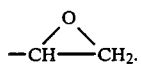

In the composition, monoepoxide compounds can be included. The aromatic polyepoxides preferably are the polyglycidyl ethers of polyhydric phenols, glycidyl esters of aromatic carboxylic acids, N-glycidylaminobenzenes, and glycidylamino-glycidyloxy-benzenes. Most preferably the aromatic polyepoxides are the polyglycidyl ethers of polyhydric phenols.

Examples of aromatic polyepoxides, useful in the epoxy resin composition of the invention, include the polyglycidyl derivatives of polyhydric phenols such as 2,2-bis-[4-(2,3-epoxypropoxy)phenyl]propane and those described in U.S. Pat. Nos. 3,018,262 and 3,298,998 incorporated herein by reference, and in "Handbook of Epoxy Resins" by Lee and Neville, McGraw-Hill Book Co., New York (1967). A preferred class of poly(glycidyl ether)s of polyhydric phenols of use in the compositions of the invention are the diglycidyl ethers of bisphenol that have pendent carbocyclic groups such as those described in U.S. Pat. No. 3,298,998, which is incorporated herein by reference. Examples of such diglycidyl ethers are 2,2-bis[4-(2,3-epoxypropoxyl)-phenyl]norcamphane and 2,2-bis[4-(2,3-epoxypropoxy)-phenyl]decahydro-1,4,5,8dimethanonaphthalene. A much preferred diglycidyl ether is 9,9-bis[4-(2,3-epoxy-propoxy)phenyl]fluorene.

Examples of N-glycidylaminobenzenes suitable for use in the epoxy resin composition of the invention include the di and polyglycidyl derivatives of benzenamine, benzene diamines, naphthylenamine and napthylene diamine such as N,N-diglycidylbenzenenamine, N,N-diglycidylnaphthalenamine [given the name of N-1-naphthalenyl-N-(oxiranylmethyl)-oxiranemethanamine by Chemical Abstracts 9th Coll. 8505F(1982–79)], 1,4-bis(N-glycidylamino)benzene, 1,3-bis(N,N-diglycidylamino)benzene, and bis[4-(N,N-diglycidylamino)phenyl]methane (MY ™ 720, Ciba Geigy, Inc.) The polyglycidyl derivatives of aromatic aminophenols are described in U.S. Pat. No. 2,951,825. An example of these compounds is N,N-diglycidyl-4-glycidyloxybenzenamine (ERL ™ 0510, Ciba Geigy, Inc.)

Examples of the glycidyl ethers of the invention (the structural formulae of those examples designated a), b), c), and d) are shown below) include:
9-[4-(2,3-epoxypropoxy)phenyl]-9-[3-methyl-4-(2,3-epoxypropoxy) phenyl]fluorene (a)
9,9-bis[3-methyl-4-(2,3-epoxypropoxy)phenyl]fluorene (b)
9-[4-(2,3-epoxypropoxy)phenyl]-9-[3,5-dimehtyl4-(2,3-epoxypropoxy)phenyl]fluorene
9,9-bis[3,5-dimethyl-4-(2,3-epoxypropoxy)phenyl]fluorene
9-[3-methyl-4-(2,3-epoxypropoxy)phenyl]-9-[3,5-dimethyl-4-(2,3-epoxypropoxy)phenyl]fluorene
9-[4-(2,3-epoxypropoxy)phenyl]-9-[3-chloro-4(2,3-epoxypropoxy)phenyl]fluorene
9-[3-chloro-4-(2,3-epoxypropoxy)phenyl-9-[3,5-dichloro-4-(2,3-epoxypropoxy)phenyl]fluorene
9-[3-chloro-4-(2,3-epoxypropoxy)phenyl]9-[3,5-dichloro-4-(2,3-epoxypropoxy)phenyl]fluorene
9,9-bis[3-bromo-4-(2,3,-epoxypropoxy)phenyl]fluorene
9,9-bis[3,5-dibromo-4-(2,3-epoxypropoxy)phenyl]fluorene
9,9-bis[3-t-butyl-4-(2,3-epoxypropoxy)phenyl]fluorene (c)
1-chloro-9,9-bis[3-methyl-4-(2,3-epoxypropoxy)-phenyl]fluorene
2-methyl-9,9-bis[3-methyl-4-(2,3-epoxypropoxy)-phenyl]fluorene
2,6-dimethyl-9-[3-methyl-4-(2,3-epoxypropoxy)-phenyl]-9[3,5-dimethyl-4-(2,3-epoxy-propoxy)-phenyl]fluorene 1,2,3,4,5,6,7,8-octafluoro-9,9-bis[3-methyl-4(2,3,-epoxy-propoxy)phenyl]fluorene (d)

2,7-dinitro-9,9-bis[3-methyl-4-(2,3,-epoxypropoxy)-phenyl]fluorene 2,acetyl-9,9-bis[3,5-dimethyl-4-(2,3-epoxy-propoxy)phenyl]fluorene 2,7-diphenyl-9-[3-methyl-4-(2,3-epoxypropoxy)-phenyl]-9[3,5-dimethyl-4-2,3-epoxy-propoxy)-phenyl]fluorene.

(a)

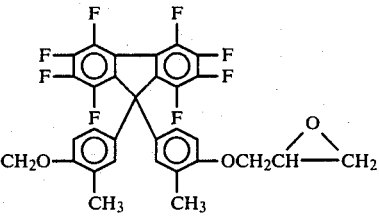

(d)

An example of a mixture of glycidyl ethers of the invention is:

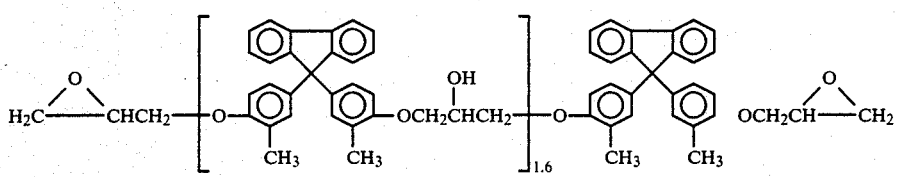

(b) 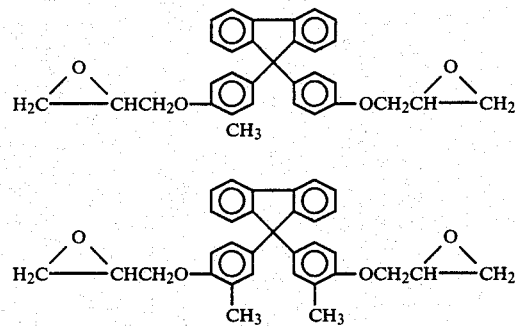

(c) 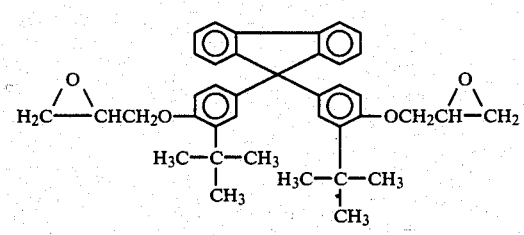

The glycidyl ethers of the invention are prepared, generally, in two steps by procedures known in the art. Step 1 consists of the preparation of the orthosubstitued fluorene bisphenols. The substituted bisphenols can be prepared by two methods. One method of preparing these materials is by the condensation of one or a mixture of two or more ortho-substituted phenols or a mixture of an unsubstituted phenol and one or more ortho-substituted phenols with fluorenone or a substituted fluorenone to yield an ortho-substituted bisphenol or mixture of ortho-substituted bisphenols. (Step 1) Ortho-substituted fluorene bisphenols can also be prepared by the modification of unsubstituted fluorene bisphenols. For example, 9,9 bis(4-hydroxyphenyl)fluorene can be reacted with a halogen to substitute a halogen at the ortho position. In step 2, the ortho-substituted bisphenol or mixture is then caused to react with an excess of epihalohydrin to yield one or a mixture of diglycidyl ether of 9,9-bis(ortho-substituted4-hydroxyphenyl)fluorenes that, if desired, can be separated by chromatography or fractional crystallization. Schematically, the two steps are:

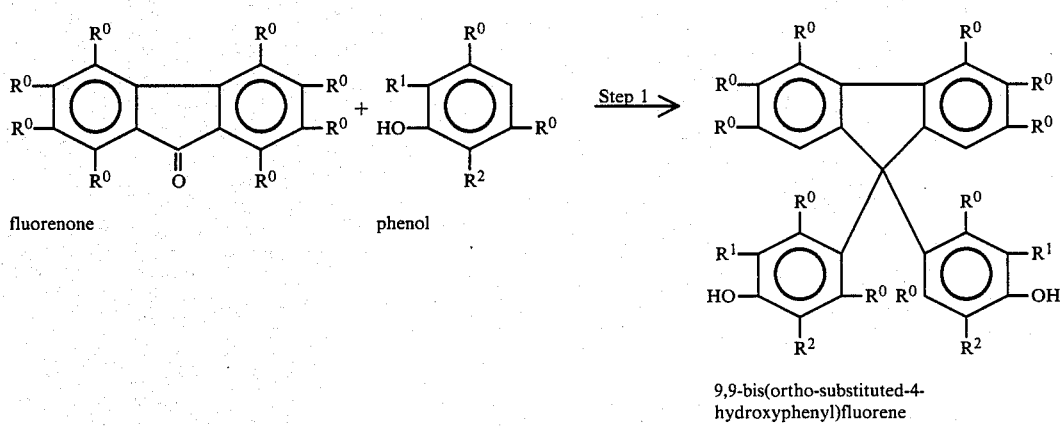

9,9-bis(ortho-substituted-4-hydroxyphenyl)fluorene

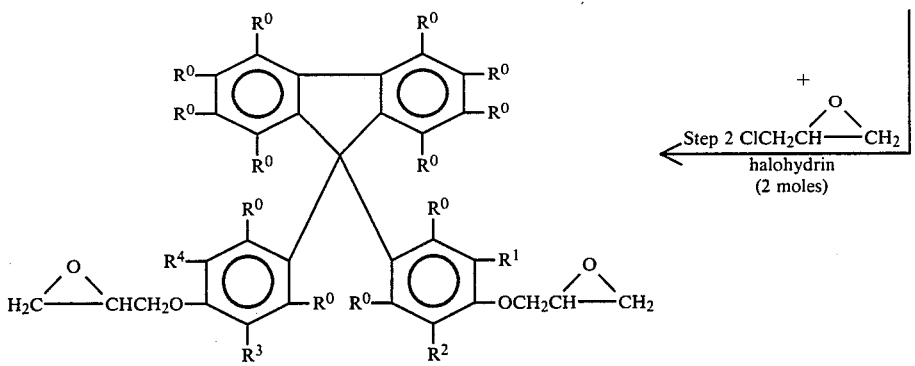

wherein each $R^0$ and $R^1$–$R^4$ are defined above.

Step 1, preferably, is carried out by agitating in a reaction vessel one mole of fluorenone, substituted fluorenone or mixture of fluorenones with two or more moles (the excess above two moles being used as solvent) of ortho-substituted or unsubstituted phenol and heating the mixture to 25° to about 125° C. in the presence of 0.1 to 1.0% based on total weight of 3-mercaptopropionic acid. The temperature of the agitating mixture is held at 25° to about 100° C. until the disappearance of the carbonyl group as can be shown by infrared spectra, generally from about 10 minutes to 10 hours. During the heating period anhydrous hydrogen chloride is passed through the agitating mixture until about one to ten weight percent of HCl based on total weight has been added. After the reaction period, the fluorenebisphenol reaction product is isolated by distillation of excess phenols and 3-mercaptopropionic acid, by chromatography, or preferatly by charging into a solvent for phenol, such as methanol, ethanol, or acetone from which the fluorene bisphenol precipiates and may be purified, if desired by working with solvent or redissolving and reprecipitating. Where mixed fluorene bisphenols are obtained they may be separated into individual compounds by methods such as chromatography. It is preferable that the unseparated mixture of fluorenebisphenol be used in Step 2.

Step 2 can be carried out in a reaction vessel having means for agitation, adding fluids and vacuum distillation. Into the vessel is added the fluorenebisphenol of Step 1, about two to ten moles of epihalohydrin, preferably, epichlorohydrin and, when needed, a solvent such as methanol, ethanol, or 1-methoxy-2-propanol in an amount, e.g., up to about twice the weight of fluorenebisphenol, necessary to insure solution of the fluorenebisphenol. The temperature of the mixture is raised to 50° to 100° C. and about 0.8 to 2.5 moles of concentrated (40 to 50 percent by weight) strong aqueous base, e.g. sodium hydroxide or potassium hydroxide is added over a period of 0.5 to 5 hours while continuously removing water under reduced pressure (e.g. about 10 to 50 Torr). These conditions are held until analysis indicates the disappearance of the phenolic hydroxy group, generally from 0.5 to 5 hours after the completion of the addition of base. The reaction mixture is filtered to remove alkali halide. Excess epihalohydrin and solvent are removed under vacuum. The product, diglycidyl ether of 9,9-bis(ortho-substituted-4-hydroxyphenyl)-flurorene can then be used directly in the compositions and articles of the invention or, where it is a mixture, it can be, if desired, separated into individual diglycidyl ethers by fractional crystallization or chromatography.

Preferably, the diglycidyl ethers of the invention for use in the curable composition of the invention are the mixtures obtained by the reaction of epihalohydrin with mixtures of fluorenebisphenols obtained by the reaction of one mole of one or more fluorenones as defined in Step 1 with two or more moles of mixtures of equal amounts of two or more ortho-substituted phenols. The diglycidyl ether mixtures from some of such ortho-substituted phenol mixtures are amorphous and therefore have better solubility in curable epoxy resin compositions than have diglycidyl ethers of any one fluorenebisphenol that are highly crystalline.

Epoxy resin curing agents and catalysta that can be used in the curable epoxy resin composition of the invention are well known in the art. Included among such curing agents and catalysts are aliphatic and aromatic primary or secondary amines as, for example di(4-aminophenyl)sulfone, di(4-aminophenyl)ether, and 2,2-bis(4-aminophenyl)propane, aliphatic and aromatic tertiary amines such as dimethylaminopropylamine and pyridine, boron trifluoride complexes such as $BF_3$-diethylether and $BF_3$-monethanolamine imidazoles such as 2-ethyl-4-methyl-imidazole, hydrazides such as adipodihydrazide, guanidines such as tetramethyl guanidine, and dicyandiamide.

Also useful as catalysts or supplementary catalysts are Lewis acids such as aluminum chloride, aluminum bromide, boron trifluoride, antimony pentafluoride, phosphorous pentafluoride, titanium tetrafluoride and the like. It is also desirable at times that these Lewis acids be blocked to increase the latency of compositions containing them. Represenative of blocked Lewis acids are $BF_3$-monethylamine and the adduct of $HSbF_5X$ in which X is OH, halogen, or $OR^8$ in which $R^8$ is an aliphatic or aromatic group with aniline or a hindered amine as is described in U.S. Pat. No. 4,503,211.

Other curing agents that can be used in the curable epoxy resin composition are one or more of 9,9-bis-(aminophenyl)fluorenes such as are described in Assignee's copending patent application U.S. Ser. No. 830,552, filed Feb. 18, 1986. Examples of these curing agents are 9,9-bis(4-aminophenyl)fluorene, 9,9-bis(4-methylaminophenyl)fluorene, 4-methyl-9,9-bis(4-methylaminophenyl)fluorene, 9,9-bis(3-methyl-4aminophenyl)fluorene, 9,9-bis(3,5-dimethyl-4-aminophenyl) fluorene, and 9-(3,5-dimethyl-4-methylaminophenyl)-9(3,5-dimethyl-4-aminophenyl fluorene.

The curable epoxy composition of the invention is prepared by mixing one or more aromatic polyepoxides of which at least 25 percent by weight is a diglycidyl ether of one or more 9,9-bis(ortho-substituted-4-hydroxyphenyl) fluorene and one or more epoxy curing agents. Where the curing agent is an amino compound there is generally used an amount of amino compound to provide equivalent concentration of amine hydrogen and epoxy groups. However, amino group-containing curing agent sufficient to provide 0.1 to 2 or more amino groups per epoxy group can be used. Where the curing agent is based on a Lewis acid, there is used from about 0.1 to 5.0 percent by weight based on total weight of the composition exclusive of any solvents. After mixing the polyepoxides and curing agents, the mixture is heated to 50° to 100° C. to liquify the mixture (it is to be noted that by the use of the ortho-substituted glycidyl ethers, liquification occurs at a lower temperature than it would occur without use of the ortho-substituted diglycidyl ethers). Heat, of course, is used to liquify the mixture only if the mixture is not already liquid or if solvents have not been used. Generally, liquification of the mixture is accomplished by dissolving it in any suitable organic solvent to form a solution having a solid content of about 25 to above about 75 percent by weight. Examples of solvents that may be used are acetone, methylethyl ketone, diisopropyl ketone and the like.

Various adjuvants can also be added to the composition of the invention to alter the characteristics of the cured composition. Included amoung useful adjuvants are thixotropic agents such as fumed silica; pigments to enhance color tones such as ferric oxide, brick dust, carbon black, and titanium oxide; filler such as silica, magnesium sulfate, calcium sulfate, and beryllium aluminum silicate; clays such as betonite; glass beads and bubbles; reinforcing material such as unidirectional woven and nonwoven webs of organic and inorganic fibers such as polyester, polyimide, glass fibers, polyamide fiber such as poly(p-phenylene terephthalamide) (Kevlar TM, E. I, duPont de Nemours and Co. Inc.), carbon fibers, and ceramic fiber. Amounts of up to about 200 parts of adjuvant per 100 parts of epoxy resin compositions can be used.

A particularly desirable adjuvant is a rubber heterophase that is introduced into the epoxy resin The rubbery heterophase can be introduced as a latex of dispersed natural or synthetic rubber as is disclosed in U.S. Pat. No. 3,316,195 or a graded rubber or core shell rubber particle as is disclosed in U.S. Pat. Nos. 3,833,683, 3,856,883, and 3,864,426. The rubbery heteropause can also be introduced into the epoxy resin composition by dissolving reactive elastomer into the epoxy resin which phase-separate during curing. The technique is exemplified by U.S. Pat. Nos. 4,107,116 and 3,894,112. A detailed discussion of the use of rubbery heteropause in epoxy resins is to be found in the Advances in Chemistry Series 208 titled "Rubbery-Modified Thermoset Resins" edited by C. K. Riew and J. K. Gillham, American Chemical Society, Washington, 1984. A preferred rubbery heterophase is the insoluble in situ polymerized elastomeric particles that are disclosed in U.S. Pat. No. 4,524,181. Generally up to about 25 parts of rubbery phase per 100 parts of epoxy resin compositions can be used.

The compositions of the invention are useful in protective coatings for various articles such as appliances, for impregnating and embedding materials for electrical components, for molding and coating applications to form shaped articles, for composite articles of woven or nonwoven webs impregnated with the composition of the invention, and other uses where the operating temperature of the article or material is elevated. The compositions of the invention are of particular use because of their unique handling properties and their high temperature performance in structural composites, filament wound articles, pultruded articles, film adhesives, printed wiring boards and the like.

Objects and advantages of this invention are further illustrated by the following examples, but the particular materials and amounts thereof recited in these examples, as well as other conditions and details, should not be construed to unduly limit this invention. In the examples all parts and percents are by weight and temperatures are in degrees centigrade unless otherwise noted.

In the examples, the glass transition temperature, Tg, was measured using a Perkin Elmer TM DSC-2 to measure the DSC midpoint. In the examples, the modulus of elasticity is measured at 20° C. using a duPont TM 1090 "Dynamic Mechanical Analyzer". Test specimens were 10.0 cm × 10.0 cm × 0.32 cm. Results were calculated to gigapascals, GPa.

EXAMPLE 1—preparation of 9,9-bis[3-methyl-4-(2-3-epoxypropoxy)phenyl]fluorene

A. Into a one liter 3-necked flask equipped with means for introducing a gas were placed
180 g fluorenone (1.0 mole)
432 g 2-methylphenol (4.0 moles)
8.0 g 3-mercaptopropionic acid (0.075 mole)

The mixture was heated to 55° C. Hydrogen chloride was bubbled below the surface for 60 minutes (18.25 g). Heating at 55° C. was then continued for 16 hours. The reaction solution was then poured into two liters of a mixture of 55 parts methanol/35 parts water. The white crystalline product which precipitated was filtered, washed with the methanol/water mixture and dried. The product was obtained in a 98% yield based on fluorenone. It had a melting point of 218°–220° C. and was confirmed by infrared spectroscopy to be 9,9-bis(3-methyl-4-hydroxyphenyl)fluorene.

B. There was added into a two liter flask equipped for addition of fluid and for distillation under vacuum
189 g of bis(3-methyl-4-hydroxyphenyl)fluorene (0.5 mole)
465 g epichlorohydrin (5.0 moles)
400 g 1-methoxy-2-propanol The mixture was heated to 65° C. and the pressure reduced to 165 Torr. There was then added over a period of 60 minutes 40 g (0.5 mole) of a 50% aqueous solution of sodium hydroxide. A continuous distillation of epichlorohydrin, 1-methoxy-2-propanol, and water took place during the base addition. The reaction mixture was allowed to cool to 25° C., the vacuum released and approximately 10 g of dry ice added to neutralize any residual base. The material that crystallized was filtered and dried. It had a melting point of 85° to 95° C. and an epoxy equivalent weight of 257. The product was confirmed by infrared spectroscopy to be a 9,9-bis[3-methyl-4-(2,3-epoxypropoxy)phenyl]fluorene of Formula I in which each R° is hydrogen, $R^1$ and $R^3$ are methyl, $R^2$ and $R^4$ are hydrogen, an n is 0.06.

EXAMPLE 2—preparation of 9,9-bis[3-chloro-4(2,3-epoxypropoxy)phenyl]fluorene

A. Into a three liter flask equipped with an agitator and means for introducing gas and a fluid were placed 175 g 9,9-bis(4-hydroxyphenyl)fluorene (0.5 mole) (prepared according to the procedure of Example 1A using an equivalent amount of phenol in place of 2-methyl-phenol) and 2000 g chloroform.

The suspension of bisphenol in chloroform was agitated and a vigorous flow of nitrogen was introduced below the surface of the liquid. Then, over a period of 45 minutes 142 g (1.05 mole) of sulfuryl chloride was added. The nitrogen flow carried the sulfur dioxide and hydrogen chloride by products into a base scrubber. The reaction was allowed to proceed for 16 hours at 22° C. During this time the suspended material disappeared and a solution formed. The solution was washed with aqueous sodium carbonate, dried over anhydrous potassium carbonate, and the chloroform removed by distillation. The product was a white crystalline material having a melting point of 165°–175° C. By liquid chromatography it was separated into 8% 9,9-bis(3-chloro-4-hydroxyphenyl)fluorene and
12% 9-(3-chloro-4-hydroxyphenyl)-9-(3,5-dichloro 4-hydroxypehnyl)fluorene.

B. The procedure of Example 1B was repeated using 210.5 g (0.5 mole) of 9,9-bis(3-chloro-4-hydroxyphenyl)fluorene in place of 189 g bis(3-methyl-4-hydroxyphenyl)fluorene. The product obtained had a melting point of 198°–202° C. and an epoxy equivalent weight of 270. The product was confirmed by infrared spectroscopy to be a 9,9-bis[3-chloro-4-(2-3,epoxypropoxy)phenyl]fluorene of Formula I in which each R° is hydrogen, R² and R⁴ are hydrogen, R¹ and R³ are chlorine, an n is 0.02.

C. When the procedure of Example 1B is repeated using 9-(3-chloro-4-hydroxyphenyl)-9-(3,5-dichloro-4-hydroxyphenyl)fluorene in place of bis)3-methyl-4-hydrophenal)fluorene, the product obtained is 9-[3-chloro-4-(2,3-epoxypropoxy) phenyl]-9-[3,5-dichloro-4-(2,3epoxypropoxy phenyl]fluorene.

EXAMPLE 3—reaction of a mixture of phenols with fluorenone and the preparation of a diglycidyl ether mixture from the fluorenebisphenol mixture obtained.

A. Into a one liter 3-necked flask equipped with means for introducing a gas were placed

| 180 g | fluorenone | (1.0 mole) |
| 188 g | phenol | (2.0 moles) |
| 244 g | 2,6-dimethylphenol | (2.0 moles) |
| 8 g | 3-mercaptopropionic acid | (0.075 mole) |

The mixture was heated to 55° C. Hydrogen chloride was then bubbled below the surface for 90 minutes (a total of 18.25 g HCl was used). The reaction was allowed to proceed for 16 hours at 55° C. during which time the color of the reacting mixture turned from the characteristic yellow color of fluorenone to deep red. The reaction mixture was then poured into two liters of a mixture of 55 parts methanol/35 parts of water whereon a fine white powder separated that was filtered off and dried. The powder had a melting point of 223° to 253° C. and was analyzed by liquid chromatography and found to be 25% 9,9-bis(4-hydroxyphenyl)fluorene,
25% 9,9-bis(3,5-dimethyl-4-hydroxyphenyl)fluorene, and
50% 9-(4-hydroxyphenyl)-9-(3,5-dimethyl-4-hydroxyphenyl)fluorene.

B. The proceeding mixture of fluorenebishphenols was converted to the corresponding diglycidyl ether mixture in accordance with the procedure of Example 1B using the fluorenebisphenol mixture in place of bis(3-methyl-4-hydroxyphenyl)fluorene. There was obtained a white powder having a melting point of 90°–105° C. and an epoxy equivalent weight of 269. The product consisted of about 25% 9,9-bis[3,5-dimethyl-4-(2,3-epoxypropoxy)-phenyl]fluorene
25% 9,9-bis[4-(2,3-epoxypropoxy)phenyl]fluorene, and
50% 9-[4-(2,3-epoxypropoxy)phenyl]-9-[3,5-dimethyl-4-(2,3-epoxypropoxy)phenyl]fluorene.

EXAMPLE 4—reaction of a mixture of 2-methylphenol and 2,6-dimethylphenol with fluorenone and the preparation of a diglycidyl ether mixture from the fluorenebisphenol mixture obtained A. The general procedure of Example 3A was followed using the reactants

| 90 g | fluorenone | (0.5 mole) |
| 108 g | 2-methylphenol | (1.0 mole) |
| 121 g | 2,6 dimethylphenol | (1.0 mole) |
| 5 g | 3-mercaptopropionic acid | |
| 15 g | anhydrous hydrogen chloride | |

There was obtained 185 g (94% of theory based on fluorenone) having a melting point of 190°–210°. By liquid chromatography confirmed by infrared spectroscopy, the product was found to be 25% 9,9-bis(3-methyl-4-hydroxyphenyl)fluorene,
25% 9,9-bis(3,5-dimethyl-4-hydroxyphenyl)fluorene, and
50% 9-(3-methyl-4-hydroxyphenyl)-9-(3,5-dimethyl-4-hydroxyphenyl)fluorene.

B. The proceeding mixture of fluorenebisphenols were converted to the corresponding diglycidyl ether mixture in accordance with the procedure of Example 1B using the fluorenebisphenol mixture in place of bis(3-methyl-4-hydroxyphenyl)fluorene. There was obtained a glassy product having an epoxy equivalent weight of 264. Analysis indicated the product to be essentially 25% 9,9-bis[3-methyl-4-(2,3-epoxypropoxy)phenyl]-fluorene,
25% 9,9-bis[3,5-dimethyl-4-(2,3-epoxypropoxy)-phenyl]fluorene, and
50% 9-[3-methyl-4-(2,3-epoxypropoxy)phenyl]-9-[3,5-dimethyl-4-(2,3-epoxypropoxy)phenyl]fluorene.

EXAMPLES 5-8—preparation of cured epoxy resins from compositions containing glycidyl ethers of ortho substituted-4-hydroxyphenylfluorenes Curable epoxy resin compositions were prepared as shown in Table I. Fifty parts of diglycidyl ether of bisphenol A were mixed with fifty parts of each of the fluorene bisphenol diglycidyl ethers and melted by heating the mixture to 120° C. To each melted mixture was added di(aminophenyl)sulfone using a 50% stoichiometric excess of NH relative to total equivalents of epoxy group present in the diglycidyl ethers. Each mixture was then vacuum degrassed and poured into a 10.0 cm × 10.0 cm × 0.32 cm verticle mold and cured by heating at 175° C. for four hours followed by two hours at 225° C. The modulus of elasticity, E, was measured using a duPont TM 982 Dynamic Mechanical Analyzer and the glass transition temperature, Tg, measured using a Perkin Elmer ™ DSC-2 using the DSC midpoint.

TABLE I

| EX No. | Glycidyl ether | (E.E.Q.)[a] | DDS[j] | | E(20° C.)[k] GPa | Tg[m] °C. |
|---|---|---|---|---|---|---|
| 5 | DEGBA[b] | (175) | PDP[c] | (269) | 43.9 | 2.96 | 223 |
| 6 | DGEBA | (175) | BMP[d] | (257) | 44.6 | 3.11 | 205 |
| 7 | DGEBA | (175) | MPDP[e] | (268) | 43.9 | 3.23 | 215 |
| 8 | DGEBA | (175) | BClP[f] | (270) | 43.8 | 3.28 | 187 |
| C[g] | DGEBA | (175) | BP[h] | (245) | 45.6 | 2.89 | 205 |

[a]epoxy equivalent of the diglycidyl ether
[b]2,2-bis[4-(2,3-epoxypropoxy)phenyl]propane
[c]mixture as prepared in Example 3 containing 25% 9,9-bis(4-hydroxyphenyl)fluorene, 25% 9,9-bis(3,5-dimethyl-4-hydroxyphenyl)fluorene, and 50% 9-(4-hydroxyphenyl)-9-(3,5-dimethyl-4-hydroxyphenyl)fluorene
[d]9,9-bis[3-methyl-4-(2,3-epoxypropoxy)phenyl]fluorene as prepared in Example 1
[e]mixture as prepared in Example 4 containing 25% 9,9-bis[3-methyl-4-(2,3-epoxy-propoxyphenyl]fluorene, 25% 9,9-[3,5-dimethyl-4-(2,3-epoxypropoxy)phenyl]fluorene, and 50% 9-[3-methyl-4-(2,3-epoxypropoxy)-phenyl-9-[3,5-dimethyl-4-(2, 3-epoxy-propoxy)phenyl]fluorene
[f]9,9-bis[3-chloro-4-(2,3-epoxypropoxy)phenyl]fluorene as prepared in Example 2
[g]comparative example in which the glycidyl ether is the glycidyl ether of a fluorene bisphenol (BP) that does not have an ortho substituting group as does the glycidyl ethers of Examples 5–8
[h]9,9-bis[4-(2,3-epoxypropoxy)phenyl]fluorene
[j]NH equivalents of diaminodiphenylsulfone (molecular weight of DDS ÷ 4 × 1.5 × epoxy equivalents of the glycidyl ether mixture)
[k]modulus of elasticity expressed in gigapascals, GPa
[m]glass transition temperature It can be observed in Table I that the glass transition temperatures, Tg, of all of the cured resins were high, e.g. 187° C. or higher, and that the modulus of elasticity, E, of each of cured resins in which there is included in the composition 50% of diglycidyl ethers of ortho-substituted-4-hydroxyphenylfluorenes was 2.96 to 3.28 GPa. The cured resin of the comparative example containing 50% of the diglycidyl ether of the unsubstituted-4-hydroxyphenylfluorene had a modulus of elasticity of only 2.89.

I claim:

1. Glycidyl ethers of ortho-substituted-4-hydroxyphenylfluorenes.

2. Glycidyl ethers of claim 1 having the formula

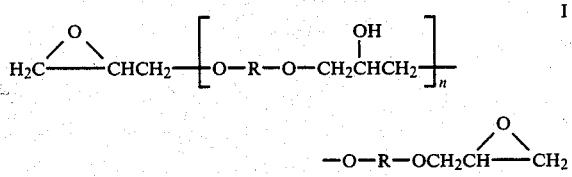

wherein n is a number having a value of 0 to 3, and R is divalent organic group having the formula

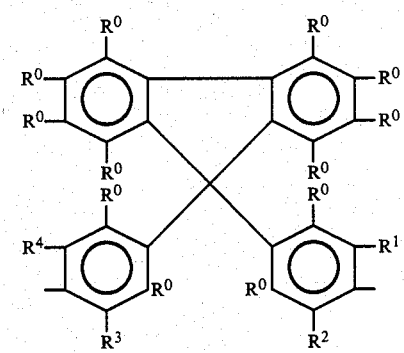

in which
each $R^0$ is independently selected from hydrogen and groups that are inert in the polymerization of epoxide group-containing compounds, and
each of $R^1$, $R^2$, $R^3$, and $R^4$ is independently selected from hydrogen, linear and branched alkyl groups having 1 to 6 carbon atoms, phenyl and halogen; with the privisos that at least one of $R^1$, $R^2$, $R^3$, and $R^4$ is a linear or branched alkyl group having 1 to 6 carbon atoms, a phenyl group, or halogen and the epoxy equivalent weight of the diglycidyl ether is at most about 500.

3. The glycidyl ether according to claim 2 wherein $R^0$ is halogen, a linear or branched alkyl group having 1 to 6 carbon atoms, phenyl, nitro, acetyl, or trimethylsilyl.

4. The glycidyl ether according to claim 2 wherein n=0.

5. The glycidyl ether according to claim 2 wherein R is derived from at least one of fluorenone or a substituted fluorenone.

6. The glycidyl ether according to claim 2 selected from the group consisting of
9,9-bis[3-methyl -4-(2,3-epoxypropoxy)phenyl]fluorene,
9,9-bis[-3,5dimethyl-4-(2,3-epoxypropoxy)phenyl]fluorene,
9,9-bis[3-chloro-4-(2,3-epoxypropoxy)phenyl)fluorene,
9-[4-(2,3-epoxypropoxy)phenyl]-9-[3-methyl-4-(2,3-epoxypropoxy)phenyl]fluorene,
9-[3-methyl -4-(2,3-epoxypropoxy)phenyl]-9-[3,5-dimethyl-4-(2-3-epoxypropoxy)phenyl]fluorene, and
9,9-bis[3,5-dibromo-4-(2,3-epoxypropoxy)phenyl]fluorene.

7. Glycidyl ethers of claim 1 prepared by the reaction of epihalohydrin with the condensation product of a mixture of two or more phenols with a fluorenone, at least one of the phenols being ortho-substituted.

8. A curable epoxy resin composition comprising
(a) at least one curable epoxy resin of which at least 25 percent by weight is a glycidyl ether of an ortho-substituted-4-hydroxyphenylfluorene; and
(b) epoxy resin curatives.

9. The composition according to claim 8 further comprising up to 75 percent by weight of other aromatic polyepoxides.

10. The composition according to claim 9 wherein said aromatic polyepoxide is at least one of a polyglycidyl ether of a polyhydric phenol, a glycidyl ester of an aromatic carboxylic acid, a glycidylaminobenzene, and a glycidylamino-glycidyloxy-benzene.

11. The composition according to claim 10 wherein said polyglycidyl ether of a polyhydric phenol is a diglycidyl ether of bisphenol having at least one pendent carbocyclic group.

12. A method comprising the steps:
(a) condensing at least one ortho-substituted phenol and optionally an unsubstituted phenol with fluorenone or a substituted fluorenone to provide at least one ortho-substituted bisphenol,
(b) reacting the resulting ortho-substituted bisphenol with an excess of epichlorohydrin to provide at least one diglycidyl ether of 9,9-bis (ortho-substituted-4-hydroxy-phenyl)fluorene, and
(c) isolating the resulting at least one diglycidyl ether of 9,9-bis (ortho-substituted-4-hydroxyphenyl)fluorene.

13. Cured resins of the curable resin composition according to claim 8.

14. Substrates impregnated or bearing a layer of the curable epoxy resin composition of claim 8.

* * * * *